United States Patent [19]
Hoffmann et al.

[11] Patent Number: 5,212,098
[45] Date of Patent: May 18, 1993

[54] BROMIDE ION DETERMINATION

[75] Inventors: Andrew F. Hoffmann, Walworth; Richard W. Bauer, Jr., Rochester, both of N.Y.

[73] Assignee: Eastman Kodak Company, Rochester, N.Y.

[21] Appl. No.: 766,944

[22] Filed: Sep. 27, 1991

Related U.S. Application Data

[63] Continuation-in-part of Ser. No. 761,181, Sep. 17, 1991, abandoned.

[51] Int. Cl.$^5$ .......................................... G01N 33/00
[52] U.S. Cl. ................... 436/125; 436/124; 436/163; 436/175; 436/178; 430/399
[58] Field of Search ............... 436/124, 125, 163, 164, 436/175, 178; 430/399

[56] References Cited

U.S. PATENT DOCUMENTS 3,329,468  7/1967  Rupe ..................................... 436/125
4,043,907  8/1977  Shimamura et al. ................. 430/399

FOREIGN PATENT DOCUMENTS 0127164  7/1983  Japan .
0135458  8/1983  Japan .
0173758  10/1984  Japan .

OTHER PUBLICATIONS

Porter, Lyman, "The Semimicro Detection of Thiocyanate and Halide Ions", Journal of Chemical Education, Aug. 1946, p. 402.

Burroughs, James E. and Alan Attia, "Consecutive Determinative of Alkali Metal Bromides and Thiocyanates in Mixtures", Anal. Chem. 40(13), Nov. 1968, pp. 2052-2053.

Kolesnikova, T. A. and R. A. Etinger, "Determination of Bromide and Thiocyanate in Developer Solutions", Tekh. Kino Telev. 12(12) 33-34, 1968, English Abstract Only.

Chemical Reviews, "Adsorption Indicators", I. M. Kolthoff, vol. 16, 87 (1935).

New Methods of Volumetric Analysis, Part VII, "Adsorption Indicators for Precipitation Titrations", K. Fajans, D. Van Norstrand Company, Inc., New York (1938).

Primary Examiner—James C. Housel
Assistant Examiner—Jan M. Ludlow
Attorney, Agent, or Firm—L. George Legg

[57] ABSTRACT

Bromide ion content in a photographic developer is an important variable to be controlled by photoprocessors who process color reversal material or color negative film. The bromide content of such developers can be determined by titration with silver ion, using tetraiodophenolsulfonephthalein (TIPS) or other suitable adsorption indicator, after the developer has been acidified with an organic acid such as citric acid. This titrimetric method can be adapted for use in a test kit which is designed for use by photoprocessors who otherwise lack the chemical sophistication to readily conduct analysis by titration, or who have the necessary sophistication, but wish to gain the benefits and convenience available from use of a test kit specifically designed for conducting the analytical method.

1 Claim, No Drawings

BROMIDE ION DETERMINATION

CROSS-REFERENCE TO RELATED APPLICATION

This invention is a continuation-in-part of application Ser. No. 07/761,181 filed Sep. 17, 1991 for Andrew F. Hoffmann and Richard W. Bauer, Jr., and entitled Bromide Ion Determination, now abandoned. The aforesaid application was designated Attorney Docket No. 62586, and mailed to the United States Patent and Trademark Office using Express Mail on Sep. 17, 1991.

FIELD OF THE INVENTION

This invention relates to quantitative chemical analysis. More particularly it relates to volumetric analysis to determine the bromide ion content of a photoprocessing solution. In a preferred aspect, such a solution is the non-chromogenic developer employed in processing silver halide-based, color reversal photographic material, e.g., film. The method involves titration of a sample of such a solution, after acidification with a suitable organic acid, e.g., citric acid. The end point of the titration is determined with a suitable adsorption indicator, such as 3',3'',5',5''-tetraiodophenolsulfonephthalein ("TIPS"), Eosin Y, or the like.

BACKGROUND OF THE INVENTION

The quality of an image prepared from color reversal materials or color negative materials can be adversely affected if the bromide content of the developer is too high. Such materials contain bromide ion, and a quantity of the bromide ion is released into the developer during processing. Hence, the bromide ion content of the developer would tend to increase during use if the developer was not replenished.

Bromide ion has an effect on the rate of development; i.e., as the bromide ion concentration increases, the time for proper development also increases. As can be seen (for example by the description of the E-6 process hereinbelow) standard process conditions specify a set time for development. Hence, in order to have an appropriate amount of development take place in the time allotted, the bromide ion content should be fairly closely controlled.

It is neither economically or environmentally sound to discard photoprocessing solutions after each use. Hence, in most photoprocessing, the formulations are used over and over again, so long as good results are achieved. It is standard practice to add fresh chemicals to seasoned photoprocessing solutions to replace chemicals that are used up during processing steps, or otherwise adjust for changes in content that occur.

Since bromide ion is an important parameter to be controlled, it is highly desirable that its content be readily determined. In sophisticated installations, bromide ion is readily determined using a silver titration and a silver electrode—reference electrode pair. However, that technique is not readily adaptable to use by many ordinary photoprocessors, since such processors generally lack the chemical sophistication and equipment needed to conduct such an analysis.

A titrimetric method using an adsorption indicator is much more adaptable to general use than a method comprising an electrometric end point determination. Silver cation titration of bromide anion in the presence of an adsorption indicator, has been known for a long time; see the references cited below. The heart of such a process is the use of the indicator, which changes color when the titration end point is reached. Adsorption indicators are well known in the art.

The use of 3',3'',5',5''-tetraiodophenolsulfonephthalein (TIPS) has been suggested as an indicator for titration of bromide with silver ion. Because of its readily distinguishable color change at the titration end point, its use is preferred in some methods for conducting this invention. However, its use is not a critical feature of the invention.

To determine the bromide ion content in a developer, it is common practice to first neutralize the developer with sulfuric acid in order to deactivate the developing agent(s) present, and prevent unwanted reaction of the developing agents with the silver titrant.

However, sulfuric acid cannot be readily adapted to a method using TIPS or other similar adsorption indicators. For such indicators to work correctly, the acid content of the solution to be titrated must be carefully controlled. In view of the high acidity of sulfuric acid, acidity control is difficult, especially at an installation which lacks the requisite chemical sophistication. Acetic acid is a weaker acid, but its use is not desired because its vapors are irritating.

Furthermore, sulfuric acid and acetic acid are both liquids. Hence, use of these acids in test kits are not preferred, since powdered reagents are preferred, when possible, for inclusion in a test kit to be used by comparatively non-skilled personnel, or to be used by sophisticated personnel who seek to gain the benefits and convenience of a test kit.

Thus, an object of unknown is to provide a titrimetric method for bromide ion content, which comprises use of an adsorption indicator, and which involves the use of an organic acid (a) with the requisite acidity, and (b) is in powder form prior to use. Such an acid must not interfere with the titrimetric method based on silver, and must also not interfere with the method used by the operator to correct for the presence of thiocyanate ion, which often is present in widely used, non-chromogenic developer formulations employed for the development of color reversal methods.

This invention satisfies the above object. Thus, this invention comprises provision of methods, which employ citric acid, or other suitable organic acid, as an acidifying agent.

Related Art

Use of fluoresceins as adsorption indicators in silver titrations was reported by K. Fajans, Z. Electrochem, 29, 495 (1923).

The technique was also described by I. M. Kolthoff, Chem. Reviews, 16, 87 (1935) and by Fajans in Chapter 7 of Newer Methods of Volumetric Analyses, W. Bottger, ed., D. Van Nostrand and Co., New York, N.Y. (1938).

SUMMARY OF THE INVENTION

This invention comprises the discovery that certain organic acids, such as citric acid can be used as an acidifying agent in the analyses of the bromide ion content of photographic processing solutions. Such solutions are exemplified by a first developer, e.g., the non-chromogenic developer, which has been employed in processing color reversal materials, e.g., film. They are also exemplified by color negative developers.

Thus in one aspect, this invention provides: in a titrimetric method for the quantitative determination of bromide ion in an aqueous solution acidified with an acid and containing bromide, which method comprises titration of said bromide ion with aqueous silver ion in the presence of an adsorption indicator; the improvement comprising acidifying said aqueous bromide-containing solution with an organic acid which is a solid at room temperature and which has an acid function with a $pK_a$ of from about 3 to about 4, and conducting said titration in the presence of said acid.

The use of citric acid in this method is especially efficacious. Citric acid is a strong enough acid to make the analysis work, but not so strong as to make acidity control difficult. Citric acid is a solid prior to use, and thereby can be made available in measured amounts in powder form, for use at photoprocessing installations which lack a high degree of chemical sophistication, or at installations who desire the use of pre-packaged reagents. Citric acid is comparatively non-toxic. Furthermore, its use does not interfere with the bromide analysis, or with corrective measures utilized to take into account the thiocyanate ion content of first developers commonly employed in processing color reversal film.

When the thiocyanate is first removed by precipitation with a copper (II) reagent, e.g., $CuSO_4 \cdot 5H_2O$ in aqueous solution, it was observed that Eosin Y gives a sharper end point than TIPS. It has also been discovered when the thiocyanate is first removed as a complex with a quaternary ammonium salt such as tetra-n-butyl ammonium hydroxide, (using a resin to adsorb the complex,) that citric acid does not interfere to a deleterious extent; and either TIPS, or Eosin Y can be efficaciously employed as an indicator in this embodiment of the invention.

It has also been discovered that the amount of citric acid employed should be maintained within certain limits for preferred results to be obtained.

Since the methods of this invention give good results, and are simple enough to be carried out by many operators in the photoprocessing industry; especially when the method is made available in test kit form, the process of this invention is readily adaptable by the user industry for which it is intended, and considered to be a significant advance in the art.

DESCRIPTION OF PREFERRED EMBODIMENTS

This invention is preferably employed to determine the bromide ion content in a developer solution which is used in the production of images from silver halide based color reversal or color negative materials. In one embodiment, it is preferred that the developer solution be the first developer, i.e., the non-chromogenic developer employed in the E-6 process described in *Manual for Processing Kodak EKTACHROME Films using E-7* (1980) *Eastman Kodak Company, Rochester, N.Y.*

In this embodiment, it is also preferred that the method be conducted in use of the test kit *Kodak Q-LAB Chemical Test Kit, Process E-6* made available by the Eastman Kodak Company, Rochester, N.Y., U.S.A., 14650.

It is also preferred that the method be employed to determine the bromide ion content in a non-chromogenic developer employed as the first developer in photoprocessing Kodak EKTACHROME color reversal film, or paper, or the developer employed in photoprocessing color negative film.

Such materials, and other color reversal materials and color negative film contain bromide ion in a form which becomes dissolved in solutions used to process such materials. Such products commonly have bromide present in the silver halide used to form a latent image upon exposure of the material to light.

Thus, in a preferred embodiment the instant invention is used with the well known, widely employed E-6 color reversal development process described in the Eastman Kodak Company manual cited above, or a substantially equivalent process. The process of this invention can also be used in conjunction with the R-3 process for color reversal paper and the C-41 process for color negative film, described below.

As well known, the first developer employed in the Kodak E-6 process contains some bromide and some iodide concentration. It also comprises a hydroxide/carbonate/bicarbonate solution having a pH @ 25° C. of about 9.65. The first developer also contains a mixture of two developing agents, and sodium thiocyanate. Anticalcium agents are also present. Prior to this invention all of such ingredients could conceivably adversely effect the methods provided by this invention. However, it has been found that this invention can be efficaciously employed on such a developer formulation, even after the formulation has been seasoned by use. Such a result could not be predicted or suggested prior to this invention.

A typical fresh tank formulation of an E-6 non-chromogenic developer for use in developing color reversal film is as follows.

TABLE I

| First developer | Fresh Tank |
| --- | --- |
| pH @ 25° C. | 9.65 ± 0.03 |
| Specific Gravity @ 27° C. | 1.062 ± 0.003 |
| Kodak Developing Agent DA-1 (Potassium Hydroquinone Monosulfonate) | 23.5 ± 1.0 g/L |
| Kodak Dimezone S Developing Agent (4-hydroxymethyl-4-methyl-1-phenyl-3-pyrazolidinone) | 1.5 ± 0.1 g/L |
| Potassium Sulfite (45% solution) | 45.5 ± 3.0 ml/L |
| Sodium Thiocyanate (51% solution) | 1.00 ± 0.05 g/L |
| Sodium Bromide | 2.54 ± 0.10 g/L (includes starter) |
| Potassium Iodide | 4.5 ± 0.5 mg/L (includes starter) |

Other components in solution: (quantities are fresh tank based on concentrate diluted to tank strength).

| | |
| --- | --- |
| Potassium Hydroxide (45% solution) | 6.5 ml/L |
| Aminotris (methylphosphonic acid), pentasodium salt, 40% solution (Kodak Antical #4) | 1.00 ml/L |
| Pentetic Acid, pentasodium salt, 40% solution (Kodak Antical #8) | 4.80 ml/L |
| Potassium Carbonate (47% solution) | 14.0 g/L |
| Sodium Bicarbonate | 12.0 g/L |

During use, the solution will gain bromide, iodide, filter dyes, adsorber dyes, sensitizing dyes, surfactants and other ingredients picked up from the film.

As is well known, the E-6 process entails processing exposed film for example, as follows:

TABLE II

| Step | Time | Solution | Function |
| --- | --- | --- | --- |
| 1 | 6 min. | First developer | develop silver |
| 2 | 2 min. | First wash | stop development |

TABLE II-continued

| Step | Time | Solution | Function |
|---|---|---|---|
| 3 | 2 min. | Reversal bath | fog silver halide |
| 4 | 6 min. | Color developer | develop silver, form dye |
| 5 | 2 min. | Conditioner | "stop" prepare for bleach |
| 6 | 6 min. | Bleach | oxidize Ag to AgBr |
| 7 | 4 min. | Fix | remove AgBr |
| 8 | 4 min. | Final wash | clean |
| 9 | 1 min. | Stabilizer | stabilize magenta coupler |

Modifications of the process can entail Step 5 comprising pre-bleaching to stabilize magenta coupler, stop, and prepare for bleach, and Step 9 comprising a final rinse to prevent water spotting.

The process of this invention comprises use with the first development step. Thus the process of this invention comprises a quality control method for the non-chromagenic developer employed to process reversal film.

Typical specifications for the aforementioned E-6 process and similar processes are as follows:

TABLE III

| Solution | Time (In Minutes) | Temperature °F. | C.° |
|---|---|---|---|
| First Developer | 6' | 100.4 ± 0.5 | 38.0 ± 0.3 |
| Water Wash 2 gal/min = 7.5 l/min | 2' | 92–103 | 33–39 |
| Reversal Bath | 2' | 75–103 | 24–39 |
| Color Developer | 6' | 100.4 ± 1.1 | 38.0 ± 0.6 |
| Conditioner | 2' | 75–103 | 33–39 |
| Bleach | 6' | 92–103 | 33–39 |
| Fixer | 4' | 92–103 | 33–39 |
| Water Wash 2 gal/min = 7.5 L/min | 4' | 92–103 | 33–39 |
| Stabilizer | 1' |  | RT* |
| Dryer |  | RT*–140° | RT–60° |

*RT = room temperature

As indicated below, this invention can be extended to bromide ion determination in color negative developers. It is preferred that the developer solution be Process C-41 Developer, and Process C-41 Developer Replenishers, described in "Manual for Processing Kodak KODACOLOR and VERICOLOR Films, Process C-42" (1984), Eastman Kodak Company.

The process C-41 entails processing exposed film for example, as follows:

TABLE III(a)

PROCESS C-41

| Step | Time Minutes (") | Solution | Function |
|---|---|---|---|
| 1 | 3'5" | Developer | Develop exposed silver, form chromogenic dye |
| 2 | 4'20" | Bleach | Oxidize Ag to AgX (X = halide ion) |
| 3 | 1'05" | First Wash | Clean |
| 4 | 4'20" | Fixer | Remove AgX (X = halide ion) |
| 5 | 3'15" | Final Wash | Clean |
| 6 | 1'05" | Stabilizer | Stabilize magenta coupler promote good drying characteristics |

Modifications of the process can entail removal of steps 3 and 5, for washless processing Process C-41B, and implementation of high agitation systems, along with Process C-41RA chemistry for rapid access processing.

The bromide test provided by this invention is intended to be used with the developer of such processes. This developer is a chromogenic developer, as opposed to the E-6 process first developer, which is a non-chromogenic developer.

The bromide test provided by this invention can be used as a process control tool for the developing step employed in the C-41 process. Specifications for the process are given below.

TABLE III(b)

C-41 Process Specifications

| Solution | Time | Temperature °F. | °C. | Comments |
|---|---|---|---|---|
| Developer | 3'5" | 100.0 ± 0.25 | 37.8 ± 0.15 | Recirculate and filter, agitate with nitrogen or turbulence |
| Bleach | 4'20" | 100.0 ± 5 | 38 ± 3 | Recirculate and filter, agitate and aerate with oil free air |
| First Wash | 1'5" | 75–105 | 24–41 | |
| Fixer | 4'20" | 100.0 ± 5 | 38 ± 3 | Recirculate and filter, agitate with oil free air, nitrogen or turbulence |
| Final Wash | 3'15" | 75–105 | 24–41 | |
| Stabilizer | 1'5" | 75–105 | 24–41 | |
| Dryer | as needed | <140 | <60 | |

The Process C-41B for washless processing, does not employ washes. The Process C-41RA employs increased agitation and more powerful bleach and fixer, in order to reduce bleach and fixer cycle time. Process C-41RA can be used with or without the wash steps as in Process C-41B. For further detail see "Using KODAK Flexicolor Chemicals", KODAK Publication Z-131, 1991 Eastman Kodak Company.

The test provided by this invention is intended for use with both tank solutions and replenishers. The KODAK offering for color negative process replenishers include:

Flexicolor Developer Replenisher
Flexicolor Developer Replenisher LORR
Flexicolor Developer Regenerator LORR Similar products of other manufacturers can be used.

The LORR replenisher and regenerator are used at half the replenishment rate of the standard developer, and therefore provide reduction in lab developer effluent. The LORR regenerator is used along with ion-exchange equipment to regenerate developer overflow, and re-use it as replenisher, at a LORR replenishment rate, and in effect results in an 80 percent re-use of developer effluent, at the LORR replenishment rate. The procedure for regeneration involves collecting the developer overflow, passing the overflow through an ion-exchange column to remove the halide ions (a basic anion exchange resin such as Rohm and Haas IRA-400 should be employed). The regenerator solution is then added to the resultant overflow from the ion-exchange treatment, adjusted to optimum pH, and then used as LORR replenisher. The result of the regeneration process, is ideally a replenisher chemically identical to LORR replenisher. This process of the invention will also work with any other manufacturer's product offerings designed for this process. The formulas of these products are described in "The Manual for Processing KODACOLOR and VERICOLOR Films", Process C-42, (1984) Eastman KODAK Company.

The typical sodium bromide levels are as follows:

| Developer Tank | 1.30 g/L ± 0.07 |
| --- | --- |
| Developer Replenisher | 0.90 g/L ± 0.05 |
| Developer Replenisher LORR | 0.45 g/L ± 0.05 |
| LORR Regenerated Replenisher | 0.45 g/L ± 0.05 |

In the analytical process of this invention, it is preferred that citric acid be employed as the sole agent used to adjust the acidity of the developer, and it is more preferred that the method of this invention be conducted (a) in the absence of added sulfuric acid, i.e., in the "substantial absence" of sulfuric acid, and (b) in the absence of added acetic acid (i.e., in the substantial absence of acetic acid").

The highly efficacious use of citric acid suggests that other organic acids which have an acidic function having a $pK_a$ of from about 3 to about 4, and which are soluble in water to an extent of at least 2 weight % at about 25° C., and which are solids at ambient temperature and pressure, and which do not interfere with the titrimetric methods of this invention, can be employed to replace all or part of the citric acid used in the preferred embodiments of this invention described herein. Thus, other acids useful as acidic agents in this invention include dicarboxylic aliphatic acids, such as succinic, glutaric, adipic, malic, dimethylmalic, cyclohexane-1,1-dicarboxylic, alphatartaric, and mesotartaric acids; substituted benzoic acids, such as m-phthalic, p-phthalic, 3-hydroxybenzoic, 3,4-dihydroxybenzoic, and 3,5-dihydroxybenzoic acids; as well as p-aminobenzosulfonic acid, gluconic acid, and the like.

The concentration of acid(s) of the types described above, should be sufficient to acidify the solution to be analyzed to a pH of about 3-4, but not so high as to introduce any appreciable positive or negative bias into the determinations, e.g., by making it difficult to visually determine the titration end point. Thus, the concentration of citric acid in the solution to be analyzed is generally from about 9 g/L to about 11 g/L, for each mL of developer in 30 mL of solution present. Similar concentrations of other acids described above can also be employed.

It is also preferred that analysis conducted in accordance with this invention be conducted at ambient temperature. As appreciated by a skilled practitioner, the titrimetric method of this invention is preferably conducted using a dispersing agent as polyvinyl alcohol to keep the silver halide formed during titration in a fine state for suspension in the aqueous system and for enhancing the ability to determine the end point of the titration.

Preferably the silver titrant is a solution of silver nitrate. Silver nitrate is a well known, water soluble compound. The invention is not critically dependent on the use of silver nitrate; any other silver salt, soluble to an appreciable extent in water, and not having a counterion or other substituent which adversely effects the analysis, can also be used.

Experimental

The methods in the present invention are preferably applied to a test kit which comprises the following:
1) A digital titrator (HACH CO., Loveland, Colo., U.S.A., Cat. No. 16900-01)
2) A digital titrator cartridge containing 0.2256 Normal silver nitrate
3) A sample pipetting device, to deliver 1.0 mL of developer sample, such as HACH CO., Cat. No. 19700-01
4) An Erlenmeyer flask, 50-mL capacity
5) 3',3",5',5"-Tetraiodophenol sulfonephthalein ("TIPS")
(The test kit may contain the citric acid and "TIPS" in a combined reagent;)
6) Polyvinyl alcohol solution, 20 g/L in water In a preferred embodiment for analyzing a Process E-6 first developer, 30 mL of deionized water is placed in the Erlenmeyer flask, 1.0 mL of the developer sample is pipetted into the flask, and 0.3 g of solid citric acid is added to the solution. The TIPS indicator is then added to the acidified developer solution, followed by 5 drops of the polyvinyl alcohol solution. The indicator can be added in the form of a 0.1% (w/v) solution, in which case 3-5 drops are used, or in the form of a coating on the citric acid granules. The solution is titrated with 0.2556 Normal silver nitrate, from the digital titrator, until the color of the solution changes e.g., from amber to greenish-gray, indicating the end point of the titration.

It is to be understood that differences in color may be observed, depending on the starting solution color; (fresh or highly seasoned developer). The combined bromide and thiocyanate, expressed as sodium bromide, can then be calculated from the following equation:

Bromide and thiocyanate, as g/L sodium
bromide = Digital titrator reading × 0.02902

The optimum amount of citric acid was experimentally determined by titrating solutions containing different amounts of citric acid, with all other components being constant. For this study, the citric acid was added in the form of a 150 g/L solution in water. The optimum amount of citric acid was defined as that required to yield acceptable accuracy with a developer sample containing a known bromide level, as well as providing a distinct end point. Initially it was observed that 1.0 mL of this solution (0.15 g citric acid) did not yield a distinct end point with fresh developer, since in this case the initial color of the indicator was not very different from the end point color, making end point detection difficult. This is due to the fact that with a lowering of the acidity level of the solution, the indicator color changes from amber to green, and the green initial color obtained with 1.0 mL of citric acid is similar to the end point color that signals completion of the titration. The data in Table IV summarize the results of this study with a seasoned developer sample containing bromide and thiocyanate equivalent to 4.02 g/L sodium bromide (as determined by standard methods). It was concluded that increasing the amount of citric acid beyond 2.0 mL of 150 g/L solution (0.3 g) caused a corresponding increase in the positive bias. Therefore, 0.3 g citric acid was chosen as the optimum amount.

TABLE IV

| mL Citric acid Solution | g Citric acid | g/L NaBr* | % of Known value |
|---|---|---|---|
| 2.0 | 0.3 | 4.10 | 102 |
| 3.0 | 0.45 | 4.14 | 103 |
| 5.0 | 0.75 | 4.18 | 104 |

*Bromide + thiocyanate expressed as NaBr; average of 4 trials

Since the desired test result is bromide ion concentration of the first developer, a means for removing the thiocyanate contribution to the titration result is necessary. Photographic processing laboratories routinely measure specific gravity of Process E-6 first developer to monitor solution concentration. A reasonable correlation between specific gravity and thiocyanate concentration was determined for solutions mixed from Kodak concentrated chemicals according to package instructions. Provided the operator properly mixes the chemicals and provided the first developer specific gravity deviates no more than 0.006 units from the specified aim value, the following relationship exists between thiocyanate concentration and specific gravity:

g/L Sodium thiocyanate=(Specific Gravity at 80 F−1.000)/0.063 or g/L Sodium thiocyanate=(Specific Gravity at 100 F−0.997)/0.063

Once the thiocyanate concentration is determined, in g/L, it must be expressed as g/L sodium bromide and subtracted from the titration result. This is done as follows:

Sodium thiocyanate (g/L)×1.269=Thiocyanate as g/L sodium bromide

To determine the solution sodium bromide concentration, the complete calculation is:

g/L Sodium bromide=(Digital Titrator Reading×0.02902)−{(SpGr at 80 F−1.000)/0.063×1.269} or g/L Sodium bromide=(Digital Titrator Reading×0.02902)−{(SpGr at 100 F−0.997)/0.063×1.269}

In a further improvement to the above test, it was found that cuprous ion would selectively precipitate thiocyanate in the presence of bromide in a developer, thus allowing the titration with silver to be selective for bromide. Furthermore, the cuprous ion could be supplied simply by the addition of a cupric salt, which generates cuprous ion in situ after reaction with the developer.

In one form of a selective bromide test utilizing this reaction, 1.0 mL of an E-6 developer sample is mixed with approximately 30 mL of deionized water in a 50-mL syringe, and 1.0 mL of 20 g/L cupric sulfate pentahydrate solution is added and mixed, followed by 0.3 g of citric acid. A syringe filter equipped with a 0.45-micrometer pore size membrane filter is attached to the syringe, and the solution in the syringe is passed through the filter into a 50-mL Erlenmeyer flask. The filtered solution in the flask is then titrated with silver titrant in the usual manner. It was observed that the fluorescein adsorption indicator, Eosin Y, yielded a more distinct end point than TIPS with this system. As an example of the data obtained with this approach, a sample of seasoned first developer containing 2.66 g/L sodium bromide yielded an experimental value of 2.66 g/L (average of 4 trials).

It was also found that the use of cuprous ion allowed a selective determination of bromide without the need for the filtration step described above. Thus, in this form of the test, 2.0 mL of 20 g/L cupric sulfate pentahydrate solution is mixed with 1.0 mL of developer and approximately 28 mL of deionized water, and 0.3 g of citric acid is added and immediately mixed with the solution. This mixture is titrated with silver ion in the usual manner to yield acceptable accuracy when either Eosin Y or TIPS is used as the indicator. For example, a seasoned developer sample containing 2.66 g/L was analyzed according to this procedure, and an average of two trials found 2.73 g/L (103% of known value).

Another method of eliminating the thiocyanate interference in the silver titration involves formation of an ion-association complex between the thiocyanate and a quaternary ammonium ion, and selective removal of this complex by means of a solid adsorbent. Specifically, the procedure involves adding 1.0 mL of the developer sample to approximately 6 mL of deionized water in a 10-mL Luer-tipped syringe, then adding 0.3 g of citric acid and 0.3 mL of 0.4 Molar tetra-n-butyl ammonium hydroxide solution, with mixing after each addition. The resulting solution is then passed through a solid-phase extraction cartridge of the type used in pretreatment of samples for liquid chromatographic analysis, containing a "C-18" bonded silica adsorbent. This type of device is exemplified by the Sep-Pak cartridge manufactured by Waters Chromatography Division, Millipore Corporation. Alternatively, a cartridge filled with a neutral poly(styrene-divinylbenzene) resin can be used, such as the OnGuard-RP from Dionex Corporation, or an equivalent. The cartridge is attached to the syringe containing the sample solution, the solution is forced through the cartridge by application of slight pressure on the syringe plunger, and the resulting eluate is collected in a 50-mL Erlenmeyer flask. The eluate in the flask is diluted to approximately 30 mL with deionized water and titrated, as outlined above, with silver nitrate in the presence of Eosin Y or TIPS indicator and polyvinyl alcohol. This procedure results in quantitative removal of thiocyanate from the developer solution and thus allows the determination of bromide alone. Table V presents results from the analysis of a fresh and a seasoned sample for bromide by this procedure.

TABLE V

| Sample | g/L NaBr Present | g/L NaBr Found* | % of Known Value |
|---|---|---|---|
| Fresh | 1.40 | 1.44 | 103 |
| Seasoned | 2.66 | 2.62 | 99 |

*Average of 3 trials

This invention can be extended to use in determining bromide ion content in other developer formulations used in color reversal processing, it also can be extended to determination of bromide ion content of developer formulations used in color negative processing.

Bromide Ion Determination in Process C-41 Developer

The test outlined previously for bromide ion E-6 developer was applied to the determination of bromide in several Process C-41 developer samples which contained known levels of bromide. In order to obtain adequate precision with Process C-41 developer, containing concentrations of bromide lower than those in the E-6 first developer, it was necessary to increase the amount of sample taken for analysis. Based on prior results with Process E-6 first developer, it was calculated that a 2.0 mL sample size would result in acceptable precision at the aim level of bromide in the standard Process C-41 developer tank solution (1.3 g/L). Therefore, the test was performed with this modification. A typical Process C-41 developer formulation is shown in Table VI. Additional details of the developer formulation can be found in "Manual for Processing Kodacolor and Vericolor Films", Process C-42 (1984), Eastman Kodak Company. Since this developer does not contain thiocyanate, the determination of thiocyanate by specific gravity measurement specified in the procedure for analyzing a developer for color reversal processing is not applied. Therefore, the sodium bromide concentration is calculated from the following equation:

g/L Sodium bromide = Digital Titrator
Reading × 0.01451

The data from the analyses of samples of this developer, containing varying levels of sodium bromide, are shown in Table VII.

TABLE VI

| Typical Process C-41 Developer | |
|---|---|
| Potassium carbonate, 47% solution | 73.1 g/L |
| Potassium bicarbonate | 2.3 g/L |
| Pentetic acid, pentasodium salt, 45% solution (Kodak Antical #8) | 8.4 g/L |
| Sodium sulfite | 3.75 ± 0.50 g/L |
| Hydroxylamine sulfate | 2.0 ± 0.50 g/L |
| Kodak Color Developing Agent, CD-4 | 4.50 ± 0.25 g/L |
| ph @ deg. C. | 10.04 ± 0.05 |
| Specific Gravity @ 27 deg. C. | 1.036 ± 0.004 |

TABLE VII

| | Bromide in Process C-41 Developer with 2.0-mL Sample Size | | |
|---|---|---|---|
| | g NaBr/L | | Precision, 1s |
| Sample | Present | Found (avg. of 4) | (g NaBr/L) |
| Fresh tank 1 | 1.00 | 1.01 | 0.016 |
| Fresh tank 2 | 1.30 | 1.31 | 0.012 |
| Fresh tank 3 | 2.00 | 2.01 | 0.009 |
| Seasoned tank | 1.24 | 1.28 | 0.014 |
| Seasoned tank with 0.23 g/L addition | 1.47 | 1.53 | 0.014 |

It was also desired to extend the application of this test to a low replenishment rate developer replenisher, which typically has a bromide concentration of 0.45 g/L. Therefore, a sample size of 4.0 mL was chosen for the testing of all Process C-41 developers, in order to ensure that the titration volumes in testing the low replenishment rate developer would be large enough to be reproducible. In addition, the amount of the combined citric acid/TIPS indicator reagent (HACH Co. "Bromide Indicator") was increased from the customary amount (one HACH Co. "Powder Pillow") to twice that amount, in order to ensure that the pH of the developer solution was reduced to the proper level. The calculation for bromide concentration was also modified to account for the change in sample volume, and it is determined by the following equation:

g/L Sodium bromide = Digital Titrator
Reading × 0.007255

A typical low replenishment rate replenisher formulation is as follows in Table VIII. Additional details of the developer formulation can be found in "Manual for Processing Kodacolor and Vericolor Films", Process C-42 (1984), Eastman Kodak Company. Data from analysis of various Process C-41 developer samples, with the 4.0-mL sample size modification, are shown in Table IX.

TABLE VIII

| Typical Process C-41 Low Replenishment Rate Developer | |
|---|---|
| Component | Typical Level |
| Potassium carbonate, 47% solution | 79.8 g/L |
| Sodium bromide | 0.45 ± 0.05 g/L |
| Potassium hydroxide, 45% solution | 3.6 g/L |
| Pentetic acid, pentasodium salt, 45% solution (Kodak Antical #8) | 8.5 g/L |
| Sodium sulfite | 4.75 ± 0.05 g/L |
| Hydroxylamine sulfate | 3.40 ± 0.25 g/L |
| Kodak Color Developing Agent, CD-4 | 5.90 ± 0.25 g/L |
| pH @ 25 deg. C. | 10.15 ± 0.04 |
| Specific Gravity @ 27 deg. C. | 1.038 ± 0.004 |

TABLE IX

| | Bromide in C-41 Developer with 4.0-mL Sample Size | | |
|---|---|---|---|
| | g/NaBr/L | | Precision, 1s |
| Sample | Present | Found (avg. of 4) | (g/NaBr/L) |
| Fresh tank 1 | 0.89 | 0.92 | 0.022 |
| Fresh tank 2 | 1.32 | 1.37 | 0.008 |
| Fresh tank 3 | 2.03 | 2.10 | 0.015 |
| Seasoned tank | 1.76 | 1.95* | 0.012 |
| Seasoned tank with 0.37 g/L NaBr addition | 2.13 | 2.34 | 0.014 |
| Low Replenishment Rate Replenisher | 0.45 | 0.47 | 0.021 |

*Sample was found to contain chloride, which contributes a positive bias to the bromide result.

Bromide Ion Determination in Process R-3 Developer

The test outlined previously for the determination of bromide in a non-chromogenic developer used for processing color reversal material was applied to the determination of bromide in R-3 Process developer samples which contained known levels of sodium bromide. A typical formulation of an R-3 Process (reversal)-/developer is shown in Table X. Since the specific gravity aim of the R-3 Process developer is different than that of the Process E-6 developer, the relationship between thiocyanate and specific gravity used in the calculation of bromide concentration in E-6 Process developer does not apply. It was therefore necessary to change the equation used for calculating bromide concentration in the R-3 Process developer to the following:

g/L Sodium bromide = (Digital Titrator
Reading × 0.02902) − ((SpGr at 80
F − 1.000)/0.061 × 1.269)

or g/L Sodium Bromide=(Digital Titrator
Reading×0.02902)−((SpGr at 100
F−0.997)/0.061×1.269)

It was observed that with seasoned R-3 Process developer, the initial color obtained after addition of the citric acid and TIPS was similar to the color obtained at the end point of the titration, making judgement of the end point more difficult than with seasoned Process E-6 developer. The data from these trials are shown in Table XI. It was subsequently found that use of a 0.5-mL sample size improved the transition between initial and end point colors, thus improving detectability of the end point. Therefore, the method was modified to use a 0.5-mL sample size, and the calculation for bromide concentration was changed to the following:

g/L Sodium bromide=(Digital Titrator
Reading×0.05804)−((SpGr at 80
F−1.000)/0.061×1.269 or g/L Sodium bromide=(Digital Titrator
Reading×0.05804)−((SpGr at 100
F−0.997)/0.061×1.269

Data from analyses of 0.5-mL samples of R-3 Process developer are shown in Table XII.

TABLE X

| Typical R-3 Process Developer Formation | |
|---|---|
| Component | Typical Level |
| Aminotris(methylphosphonic acid), pentasodium salt, 40% solution (Kodak Antical #4) | 1.41 g/L |
| Pentetic acid, pentasodium salt, 45% solution (Kodak Antical #8) | 8.25 g/L |
| Potassium sulfite (anhydrous) | 30.0 ± 2.0 g/L |
| Sodium thiocyanate (anhydrous) | 1.0 ± 0.10 g/L |
| Potassium hydroxide, 45% solution | 9.0 g/L |
| Kodak Dimezone S Developing Agent (4-hydroxymethyl-4-methyl-1-phenyl-3-pyrazolidinone) | 1.5 ± 0.1 g/L |
| Potassium carbonate | 14.0 g/L |
| Sodium bicarbonate (anhydrous) | 12.0 g/L |
| Kodak Developing Agent DA-1 (Potassium hydroquinone monosulfonate) | 23.3 ± 2.0 g/L |
| Sodium bromide | 2.4 ± 0.2 g/L |
| Potassium iodide | 0.008 g/L |

TABLE XI

| | Bromide in R-3 Process Developer with 1.0-mL Sample Size | | |
|---|---|---|---|
| | g NaBr/L | | Precision, 1s |
| Sample | Present | Found (avg. of 4) | (g NaBr/L) |
| Fresh Tank | 2.40 | 2.54 | 0.040 |
| Seasoned tank | 2.18 | 2.07 | 0.034 |

TABLE XII

| | Bromide in R-3 Process Developer with 0.5-mL Sample Size | | |
|---|---|---|---|
| | g NaBr/L | | Precision, 1s |
| Sample | Present | Found (avg. of 4) | (g NaBr/L) |
| Seasoned tank 1 | 2.18 | 2.18 | 0.13 |
| Seasoned tank 2 | 2.38 | 2.38 | 0.058 |

The data demonstrates that the test previously described for determination of bromide in non-chromogenic developer formulations for processing color reversal films can be successfully applied to the same determination in developer formulations for color negative processing and non-chromogenic developer formulations for processing color reversal paper.

The invention has been described with particular reference to preferred embodiments thereof. A skilled practitioner, familiar with the above detailed description can make many substitutions or modifications without departing from the scope and spirit of the appended claims.

We claim:

1. In a titrimetric method for the quantitative determination of bromide ion present in a non-chromogenic developer containing thiocyanate ion, the improvement comprising (a) acidifying said developer with sufficient citric acid to deactivate the developer and thereby prevent unwanted reaction of said developer with a silver ion titrant consisting essentially of aqueous silver nitrate, subsequently (b) removing thiocyanate ion as a quaternary ammonium complex by adsorbing said complex on an adsorbent; and (c) subsequently titrating said developer with aqueous silver nitrate until the end point is reached, using TIPS or Eosin Y as an indicator for said titration.

* * * * *